United States Patent [19]

Urbaniak

[11] Patent Number: 4,673,396
[45] Date of Patent: Jun. 16, 1987

[54] SYRINGE CARTRIDGE

[76] Inventor: Ray Urbaniak, 1400 NW. 4th Ct., Boca Raton, Fla. 33432

[21] Appl. No.: 648,234
[22] PCT Filed: Oct. 27, 1983
[86] PCT No.: PCT/US83/01688
  § 371 Date: Jun. 13, 1984
  § 102(e) Date: Jul. 22, 1984
[87] PCT Pub. No.: WO84/02079
  PCT Pub. Date: Jun. 7, 1984
[51] Int. Cl.[4] ............................................. A61M 5/00
[52] U.S. Cl. .................................. 604/211; 604/224; 604/187; 604/244
[58] Field of Search .................. 604/218, 199–205, 604/208, 211, 212, 236, 238, 240, 244, 224

[56] References Cited

U.S. PATENT DOCUMENTS

| | | | |
|---|---|---|---|
| 1,707,880 | 4/1929 | Sheets | 604/125 |
| 2,431,985 | 12/1947 | Bowman et al. | 604/211 X |
| 2,736,315 | 2/1956 | Feeney | 604/211 X |
| 4,044,758 | 8/1977 | Patel | 604/125 |
| 4,057,050 | 11/1977 | Sarstedt | 604/125 |
| 4,289,648 | 9/1981 | Hoskins et al. | 604/416 X |
| 4,291,701 | 9/1981 | Bowman | 604/122 |

Primary Examiner—Stephen C. Pellegrino

[57] ABSTRACT

The invention provides an apparatus which includes a syringe cartridge (10) having its open lower portion closed by a plunger piston (14). The upper portion is closed by a syringe cartridge closure (15) having a leur tip cap (50). Structure is optionally provided interiorly of the tip cap to retain a hollow needle (40), which is held in position by a leur tip (34), the latter being vented and provided with a seal for the needle. A displacement dome (38) is provided at the lower portion of the syringe cartridge closure (15) to displace a minor amount of fluid upon closure to seal the cartridge, and insure zero head space. The piston plunger (14) at the lower portion of the cartridge can be advanced, desirably by a second plunger (61), to empty the contents. Upon resealing, the leur tip cap (50) is applied over the leur tip (34) after a bead is formed on the tip. The tip cap (50) then penetrates the leur tip (34), or optionally the interior of the hollow needle (40) thus completely reclosing the cartridge and sealing the same for storage until intended for further use. Optionally, a metering screw plunger system (85,90,95,96) may be employed.

2 Claims, 42 Drawing Figures

SYRINGE CARTRIDGE

FIELD OF INVENTION

The present invention is directed to a syringe cartridge, which provides for controlled or zero head clearance with the contents, thereby isolating the contents from ambient air.

SUMMARY OF THE PRIOR ART

Measurement of human blood gases is a well known medical test and is routinely performed with specialized blood gas instruments. These instruments must be frequently tested for accuracy and calibration to insure that reliable measurements are being made. Recently the advantages of using gas equilibrated, buffered, stabilized human blood cell suspensions as quality control specimens to be run in conjunction with patient specimens have been described. See for example U.S. Pat. No. 4,126,575 to Louderback. However, such blood gas control material requires special handling, including incubation and agitation prior to use, and avoidance of contact with air.

An attempt was made by Intensive Technology, Inc. of 25 Bay State Road, Boston, Mass., in a product called "Respatrol" to minimize the above problems by sealing the blood gas control with a gel. However, the integrity of the seals as well as opening and resealing of the ampules was less than satisfactory.

It thus becomes highly desirable, in view of the prior art and the problems, to provide for zero head space in a cartridge, and continuing zero head space during the dispensing of the contents of the cartridge, particularly where whole blood or other ingredients are involved that must be sealed from ambient air. It is further desirable to accomplish such a packaging with resealable and reclosure features which constantly inhibit the ingress of air into the container. In addition, it is desirable to be able to dispense the entire contents accurately and without contamination by air after repeated usage and resealing. Where the cartridge will be used numerous times for very small microsamples, there is a possibility of drawback of ambient air, and the formation of bubbles. By micrometering with a high degree of precision, this problem can be minimized.

SUMMARY OF THE INVENTION

The present invention is directed to a cartridge which is filled and can be subsequently capped and closed. This is done by filling to a discrete level and then applying a closure. The closure bottom displaces a predetermined amount of air or gas and a small amount of product from the interior of the cartridge. The entirety of the process of filling is done in a vented environment, and the closure applied at ambient. The invention also provides a syringe cartridge having its open lower portion closed by a plunger piston. The upper portion is closed by a syringe cartridge closure having a leur tip cap. Means are optionally provided interiorly of the tip cap to retain a hollow needle, which is held in position by a leur tip, the latter being vented and provided with a seal for the needle. A displacement dome is provided at the lower portion of the syringe cartridge closure to displace a minor amount of fluid upon closure to seal the cartridge, and insure zero head space. The piston plunger at the lower portion of the cartridge can be advanced, desirably by a second plunger, to empty the contents. Upon resealing, the leur tip cap is applied over the leur tip after a bead is formed on the tip. The tip cap then penetrates the leur tip, or optionally the interior of the hollow needle thus completely reclosing the cartridge and sealing the same for storage until intended for further use. Optionally, a metered screw plunger system is employed. In this alternative embodiment where micrometering is desired, a metered screw plunger system is utilized. This permits precise samples to be withdrawn and inhibits drawback or retraction of the system which inherently is vulnerable to bubble entrapment in the solution.

In view of the foregoing it is a principal object of the present invention to provide a syringe cartridge with zero head space in the interior to eliminate ambient air. A related advantage stems from the use of the subject product with a whole blood control so that equilibration is not required.

Still another object of the present invention is to provide a syringe cartridge which permits continued re-use without contaminating the remaining contents.

Still another object of the present invention is to provide for a needle interiorly of the leur tip which is partially driven through the plastic membrane of the closure, to thus avoid plugging the needle due to coring of the needle opening.

Yet another object of the present invention is to minimize the force required to drive the needle by providing seal ribs interiorly of the leur tip, and yet retain the sealing function required to inhibit leakage around the needle.

A further object of the invention is to provide a syringe cartridge which is adaptable to utilization directly as a syringe by applying a hypodermic needle on the leur tip.

Still another important object of the present invention is to provide a syringe cartridge which is simple and efficient to fill, and which inhibits contamination of the contents from ambient air.

Another objective is to prepare a syringe cartridge and method for using the same which can be used with a wide variety of chemicals and reagents where controlled or zero head space is required to maintain the stability and activity of the contents.

Desirably precise control and metering of the contents is provided by a metered screw plunger system.

BRIEF DESCRIPTION OF THE DRAWINGS

Further objects and advantages of the present invention will become apparent as the following description of an illustrative embodiment and method proceeds, taken in conjunction with the accompanying drawings, in which.

DESCRIPTION OF THE FIRST EMBODIMENT

Figure 1:
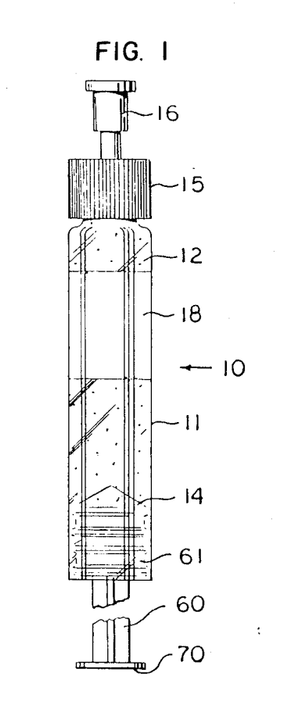
FIG. 1 is a front elevation of an illustrative syringe cartridge showing its principal elements as the product is sold to a typical user.

The first embodiment syringe cartridge is shown in FIG. 1, where it will be seen that it has an elongated cartridge body 11, and filled with contents 12. A plunger piston 14 seals off the lower portion of the cartridge 11, and a syringe cartridge closure 15 is provided at the top. The syringe cartridge closure 15 has a leur tip cap assembly 16 which completes the closure. Shown also is a wrap around label 18.

Figure 2:
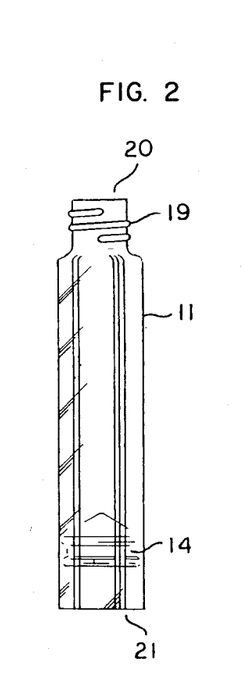
FIG. 2 is a front elevation in essentially the same scale as FIG. 1 showing the cartridge in its initial position prior to filling.

Turning to FIG. 2, it will be seen that the first step in assembling the syringe cartridge 10 is to provide a cartridge 11, preferably a sterilized glass tubular member, with the plunger piston 14 in place. To be noted is the upper portion of the cartridge 11 is provided with a thread finish 19, terminating in an open filling end.

Figure 3:
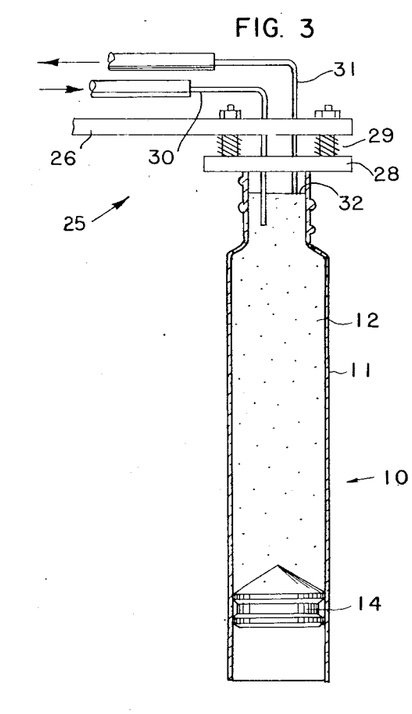
FIG. 3 shows the cartridge with its filling station as the same is being filled.

The next step illustrated in FIG. 3 is to fill the cartridge 11 with contents 12 in a drawback system. This is accomplished essentially by providing a filler head assembly 25 having a support bar or filler bar 26, and a cartridge cover 28 supported by a spring loaded suspension 29 from the filler support bar 26. A contents tube 30 is provided to penetrate through the cartridge cover 28 and dispense contents 12 into the cartridge 11. At the same time, a vent tube 31 is employed to permit the ambient atmosphere and excess product inside the cartridge 11 to be dispelled as the contents 12 are inserted. Pragmatically as well as theoretically, a precise controlled fill level 32 is calculated so that when the syringe cartridge closure 15 is applied, there will be an essentially total head space displacement, and the interior portion of the cartridge 11 will be solely occupied by its contents 12.

Figure 4:
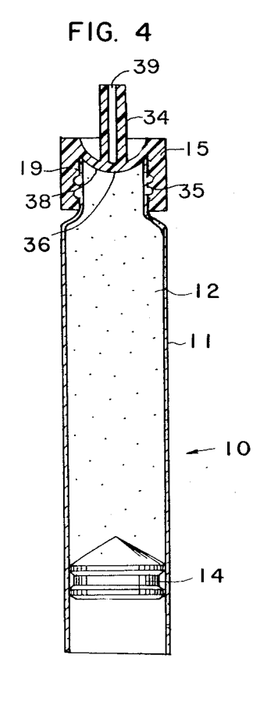
FIG. 4 discloses the filled cartridge after being filled in accordance with FIG. 3 and having the closure applied.
Figure 5:
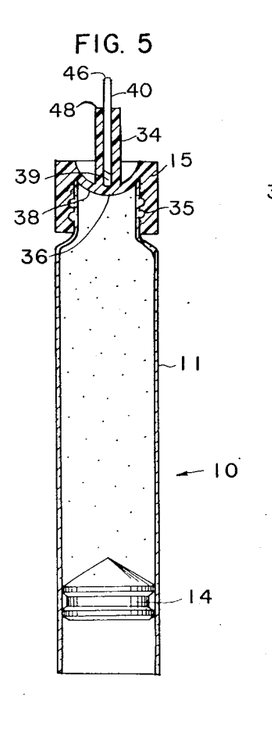
FIG. 5 discloses the next sequence in which the needle is inserted into the leur tip.

As shown in FIG. 4, when the closure 15 is applied to the threaded finish 19 of the cartridge 11, there is an observable leur tip 34, at the bottom of which is a diaphragm 36, from which extends the dome of the content displacement portion of the closure 15. The leur tip 34 also defines a leur tip needle bore 39 in its interior portion. The threaded finish 19 of the bottle along with the interior threads of the closure 15 form a contents displacement trap, which will become apparent as the closure 15 is subsequently described in greater detail along with drawings of more specific details. In closing the contents displacement trap 35 a small amount of the contents 12 will spill over but be trapped a the threaded joints between the closure 15 and the threaded finish 19 of the upper portion of the cartridge.

Figure 6:
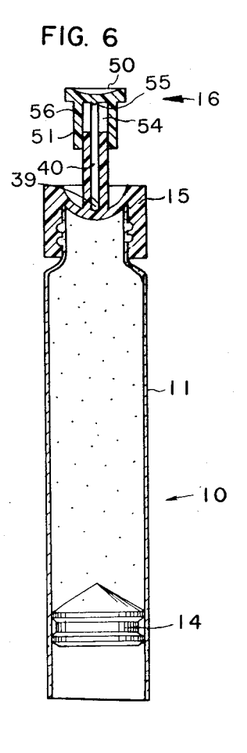
FIG. 6 is a further sequential view in which the leur tip cap is applied to the cartridge.
Figure 7:
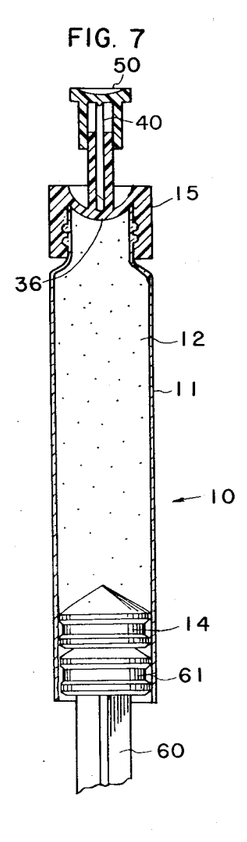
FIG. 7 shows the first step in preparing the cartridge for usage by inserting preferably a second shaft piston and plunger, and the same is now ready for shipment to the customer.
Figure 8:
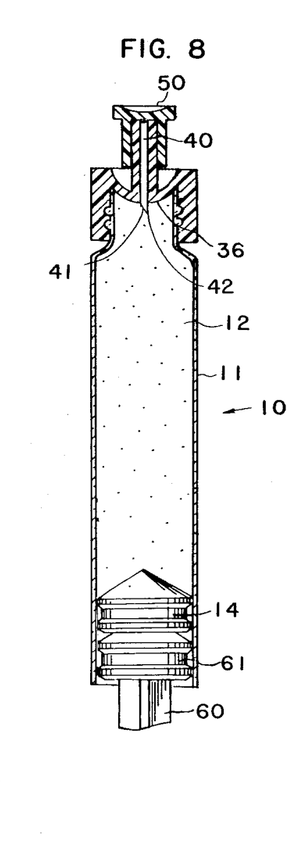
FIG. 8 shows the second step in which the leur tip cap is depressed, and the needle penetrates a diaphragm providing open communication with the contents of the cartridge.
Figure 18:
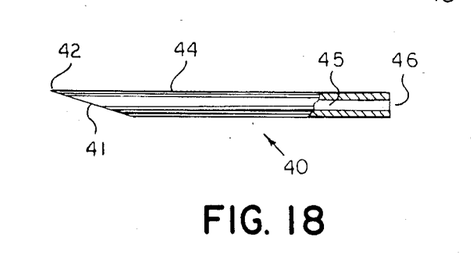
FIG. 18 is a front elevation of the needle in enlarged scale and showing its principal components.

As shown in FIG. 6, a hollow needle 40 is subsequently inserted into the leur tip needle bore 39. The needle 40, as shown in specific detail on FIG. 18, shows the termination at one end with a bevel 41 defining a point 42. The shank 44 of the needle contains a bore 45 which terminates at the dispensing end 46 of the needle 40. The opposite end of the bore 45 terminates at the bevel face 41 where the point 42 is defined. As will be shown, the leur tip dispensing end 48 is substantially flush with the needle dispensing end 46 when the unit is activated. FIG. 7 shown the insertion of the shaft piston 61 secured to the plunger shaft 60. The point 42 penetrates the diaphragm 36 (as shown in FIG. 8) but the bevel 41 only partially penetrates the diaphragm 36 to reduce any tendency for coring which would plug the needle 40.

Figure 9:
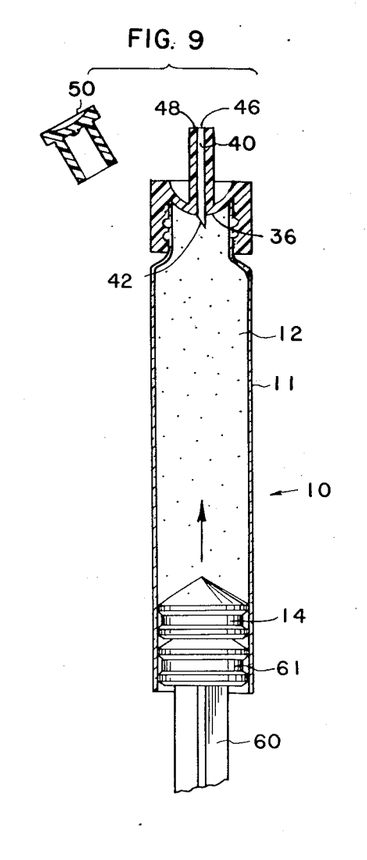
FIG. 9 is the next sequential view of the user showing the leur tip cap being removed, and pressure applied to the plunger piston and plunger shaft to dispense the contents of the cartridge.
Figure 10:
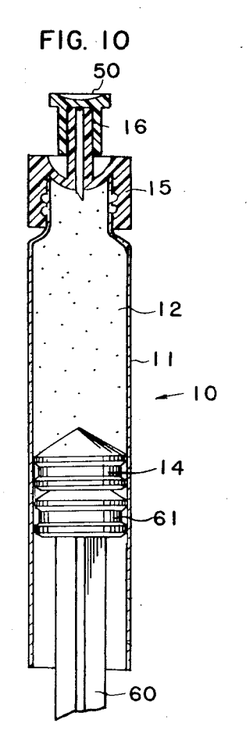
FIG. 10 shows a further sequential view in which the leur tip cap is placed in position on the needle and the leur tip, thus sealing the same for storage and re-use.
Figure 11:
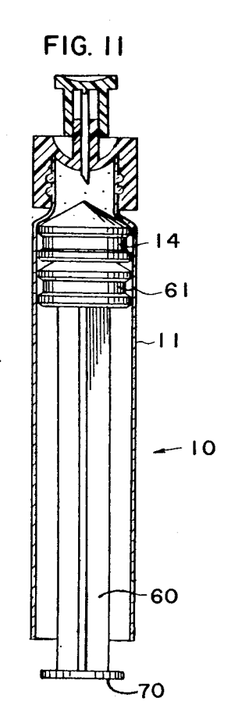
FIG. 11 shows the condition of the cartridge and contents after the syringe or cartridge is virtually depleted of its contents, and the upper piston can no longer function.

Referring now to FIG. 9, after the needle 40 has been pressed into the contents and the tip 42 has penetrated the diaphragm 36 and is in contact with the contents 12 of the cartridge 11, the leur tip cap 50 is removed. Pressure is applied to the plunger 14, and the product then injected in accordance with the particular control coupler required. Alternatively the product can be dispensed into an intermediate container to be later drawn into the aspirating instrument. Upon conclusion of the dispensing, a small bead of contents 12 is formed at the top of the needle dispensing end 46 flush with the dispensing end 48 of the leur tip. Thereafter, as shown in FIG. 10, the technician replaces the leur tip cap and the syringe cartridge 10 is ready for storage until it is to be reused again. Finally, as shown in FIG. 11, the plunger piston 14 ultimately reached a point in the neck of the cartridge 11 where no more contents can be dispelled, and the syringe cartridge and its contents are ready for disposal.

Figure 12:
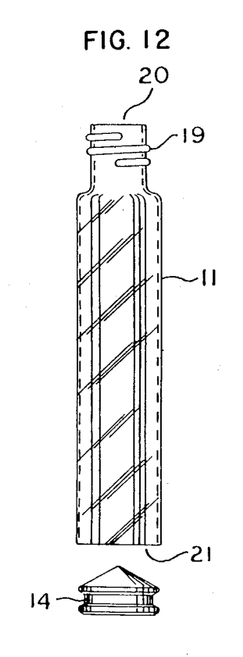
FIG. 12 is a front elevation of the syringe cartridge.

In greater detail, it will be seen in FIG. 12, that the syringe cartridge 11 has a thread finish 19 at one end, which is the filling end 20. The opposite plunger end 21 is flame polished left open and receives the plunger 14.

Figure 13:
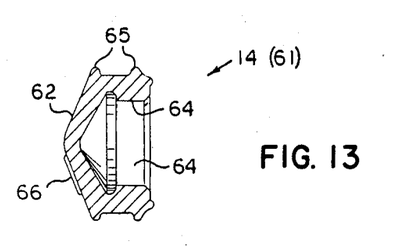
FIG. 13 is a transverse sectional view of the plunger piston.

In FIG. 13 the plunger piston 14 is shown having a dome 62. Interiorly a piston shaft lock colar 64 is provided to receive the piston shaft which will be described later. Exteriorly, a pair of seal rings 65 are shown which engage the interior wall of the cartridge 11. Optionally the dome 62 and ribs 66 of the shaft piston engage the base of the lock collar 64 of the plunger piston 14.

Figure 14:
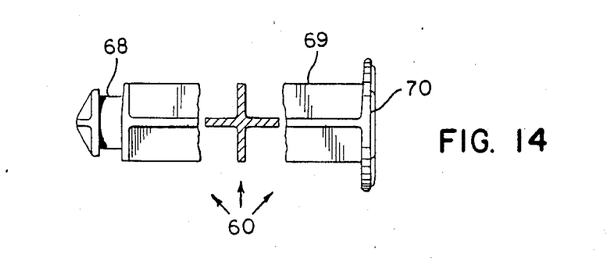
FIG. 14 is a front elevation partially in section of the plunger shaft.

Turning now to FIG. 14, the basic structure of the plunger shaft 60 is shown, and more specifically the connector head 68 which couples with the lock colar 64 of the plunger piston 14. The body 69 separates the connector head 68 from the thumb plate 70, which is used by the technician to activate the displacement of the contents 12 from the cartridge 11.

Figure 15:
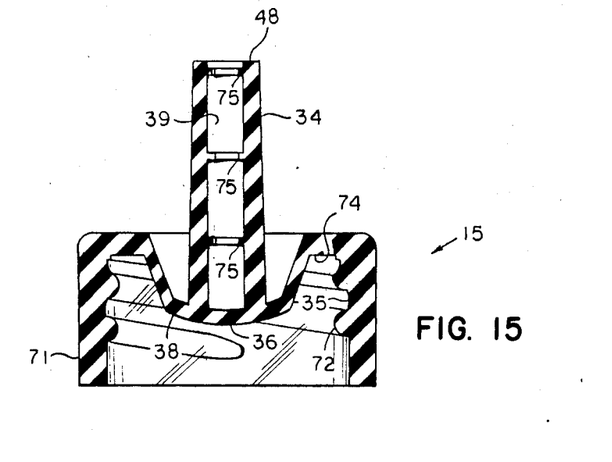
FIG. 15 is a transverse sectional view of the syringe cartridge closure.

The syringe cartridge closure 15 is shown in detail in FIG. 15. There it will be seen that the upper portion of the leur tip 34 terminates in a dispensing end 48. The leur tip 34 has an interior leur tip bore 39. The dome for product displacement 38 is shown at the bottom of the leur tip 34, and centrally it will be seen that a diaphragm 36 is provided for penetration by a needle 40. The contents displacement trap 35 is defined by the interior threads 72 of the skirt 71 which terminate in a seal at the interior of the upper portion of the skirt 71.

Figure 16:
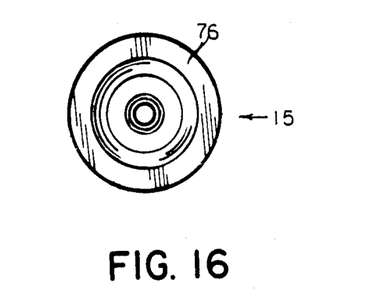
FIG. 16 is a top view of the syringe cartridge closure showing the closure ribs employed for machine torquing.
Figure 17:
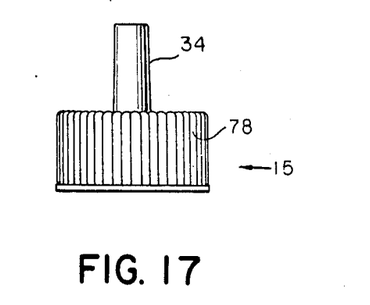
FIG. 17 is a front elevation of the syringe cartridge closure showing the knurled rim ribs for finger tightening.

As shown in FIG. 16, closure ribs 76 are provided above the seal portion 75 for machine torquing of the closure 15 onto the cartridge 11. As shown in FIG. 17, the closure 15 has knurled skirt ribs 78 to assist in hand tightening.

Figure 19:
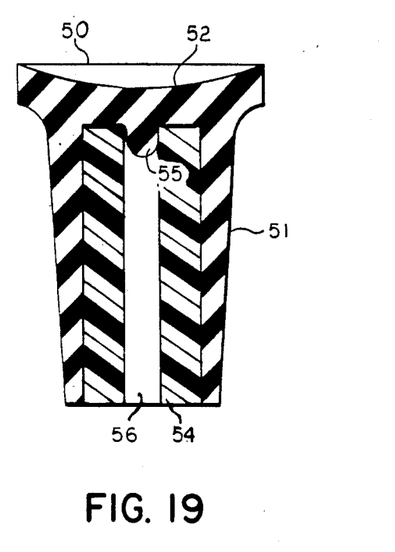
FIG. 19 is a transverse sectional view in enlarged scale of the leur tip cap.
Figure 20:
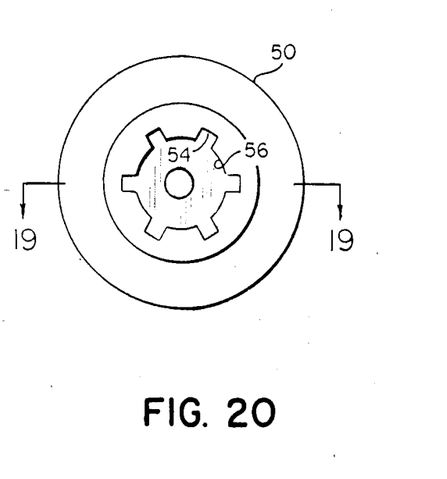
FIG. 20 is a bottom view of the leur tip cap showing the vent channels and the leur tip grip.

Finally, the leur tip cap 50 is shown in FIGS. 19 and 20. Turning specifically to FIG. 19, it will be seen that the leur tip cap 50 has a body portion 51, terminating in a thum plate 52. In the interior portion of the body 51 means are provided to define vent channels 54, separating leur tip grips 56. A needle seal 55 is formed beneath te central portion of the thumb plate 52, and proportioned to fit into the dispensing end 46 of the needle upon reclosure. Another view of the vent channels end 54 and leur tip grip 56 appear in FIG. 20.

SECOND MICROMETERING EMBODIMENT

Figure 21:
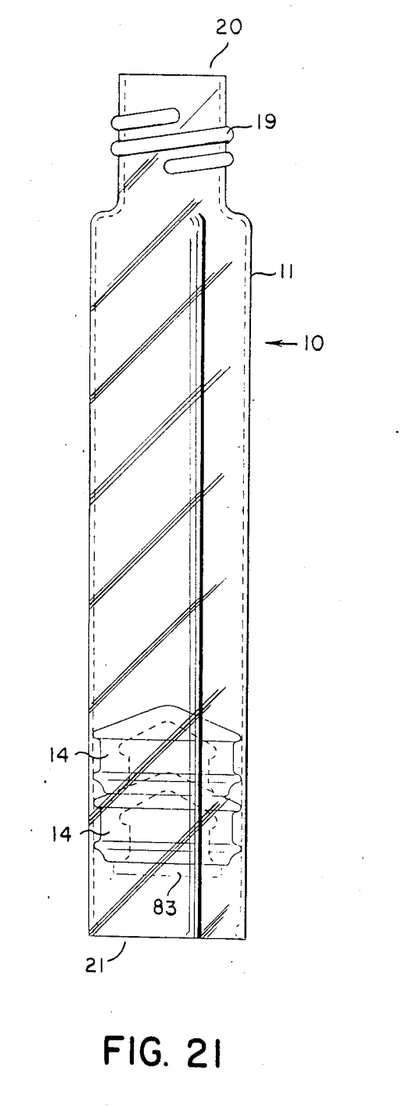
FIG. 21 is a front elevation of the alternative micrometering embodiment as shown in FIGS. 21–36 with two plunger pistons and a plunger piston insert shown in phantom lines positioned prior to filling.
Figure 36A:
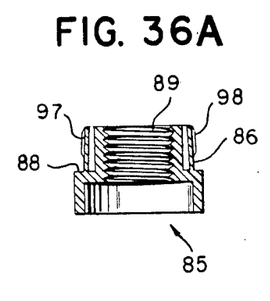
FIGS. 36A and 36B are a composite view of the adapter showing the details of securing the same to the cartridge.
Figure 36B:
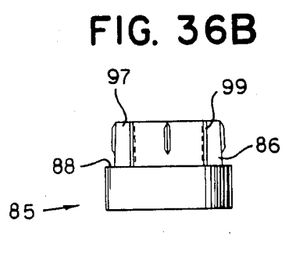

The micrometering embodiment disclosed in FIGS. 21 through 36 will be described using common reference numerals when the same are common. Turning now to FIG. 21, it will be seen that the syringe cartridge 10 along with its cartridge body 11 and thread finish 19 terminating at the filling end 20 and flame finished plunger end 21 are essentially the same. At this point the cartridge is siliconized and then the two plunger pistons 14 and the plunger piston insert 83 are inserted prior to sterilizing and filling. The plunger piston insert 83 (see bottom plunger 14 of FIG. 22) is substantially identical with the connector head 68 of the plunger shaft 60 as shown in FIG. 14. The base portion has a chamfered recess 84 to be matingly engaged by the upper end of the metering screw 90 (depicted in subsequent Figures) which activates the plunger pistons 14. The screw adapter 85 as shown in cross-section in FIG. 36A has a slotted flexible skirt portion 97, and independent ribs 98. The slotted skirt portion 97 permits flexing of the end of the adapter as it is placed inside the cartridge 11, and the ribs coact with the bead formed by the flame finishing of the plunger end 21 of the cartridge glass to hold the adapter 85 in place for assembly, and prior to labelling when it is further secured in position by the label 82, FIG. 26. The bead fits into the space defined by the gap between the rib 98 and the stop 88 and around the shoulder 86. FIG. 36(B) is another view, not in cross-section, showing the balance of the details of the skirt 97 and slots 99.

Figure 23:
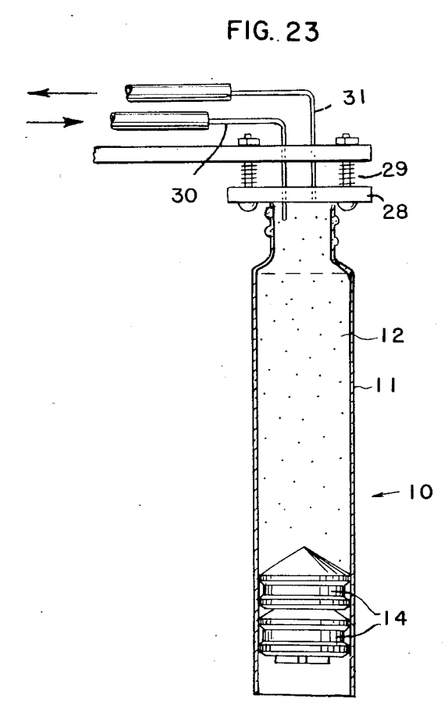
FIG. 23 shows a further front elevation of the micrometering embodiment with the contents at a 10% top off with a 360° draw-back system.
Figure 24:
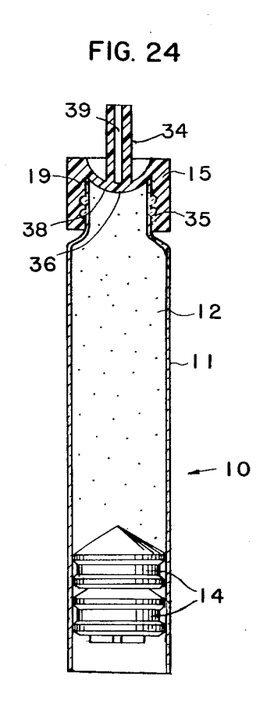
FIG. 24 is a further sequential step after the syringe cartridge closure has been positioned with zero head space.
Figure 25:
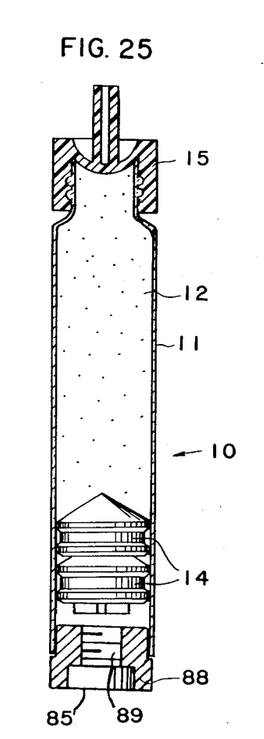
FIG. 25 is a sequential view showing the addition of the screw plunger adapter for the metering screw plunger.
Figure 26:
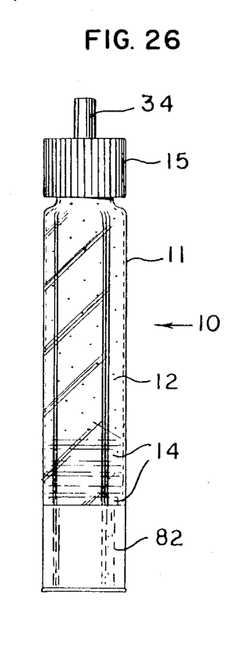
FIG. 26 is a front elevation of the micrometering embodiment showing the syringe cartridge with the label at its lower portion.

The cartridge is desirably flushed with nitrogen and 90% filled using the bottom up filler 80 from which the contents 12 are filled through the discharge 81 at the bottom of the bottom up filler 80. Then as shown in FIG. 23, a 10% top off is achieved using the cartridge cover 28 along with the spring load suspension 29 supporting the contents tube 30 and the vent tube 31 to achieve a 360° draw-back type solution and fill. At the end of this sequence, the entire contents 12 are inside the cartridge 11. Thereafter, as shown in FIG. 24, the syringe cartridge closure 15 is applied to cap the contents 12 with zero head space. Subsequently, as shown in FIG. 25, the screw plunger adapter 85 is inserted at the lower portion of the cartridge 11, terminating the end of the pressing of the shoulder 86 to the stop 88. As is noted, the screw adapter 85 has an interior thread 89. The unit is then completed as shown in FIG. 26 by placing a label 82 on the barrel which optionally has a shrink under portion to secure the screw adapter 85 in place, hidden from view by label 82.

Figure 27:
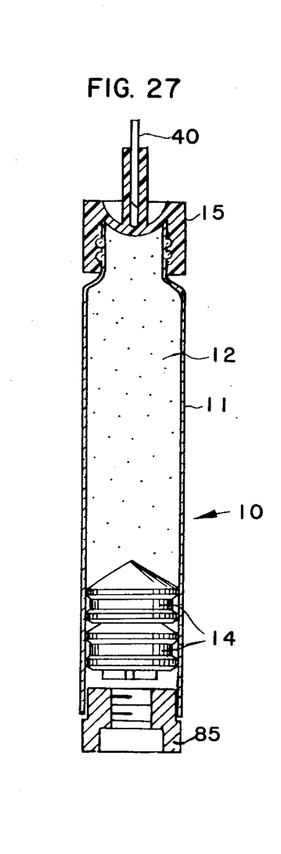
FIG. 27 shows the syringe cartridge with the needle in place.
Figure 28:
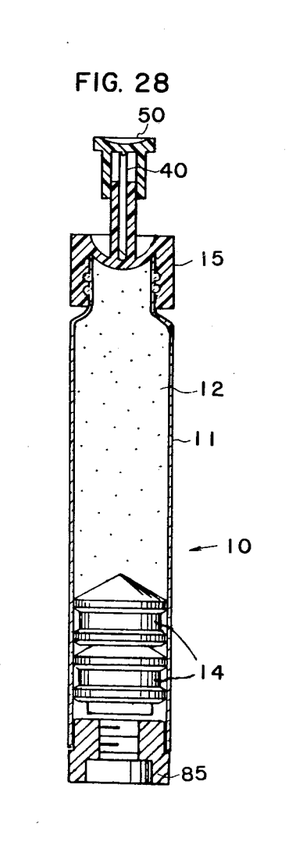
FIG. 28 shows the piston with the sterilized leur tip cap 50 in place.
Figure 29:
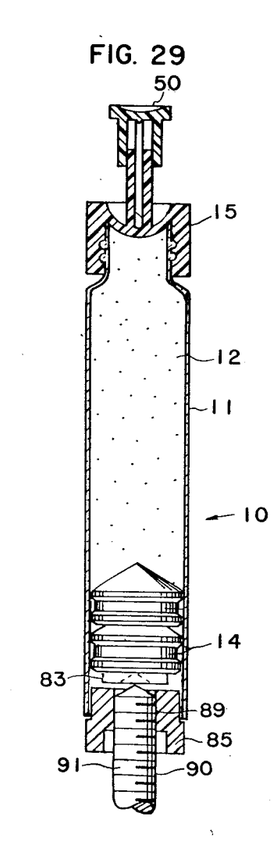
FIG. 29 shows a sequential view in which the metering screw plunger is readily engaged to the screw plunger adapter ready for shipment and use.
Figure 30:
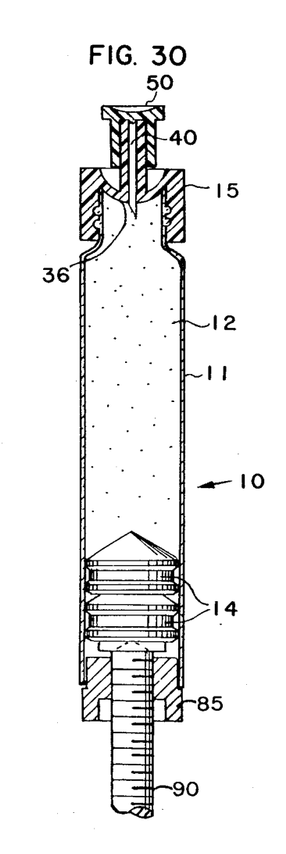
FIG. 30 is a further front elevation of the syringe cartridge with the membrane of the syringe cartridge closure pierced by the needle.
Figure 31:
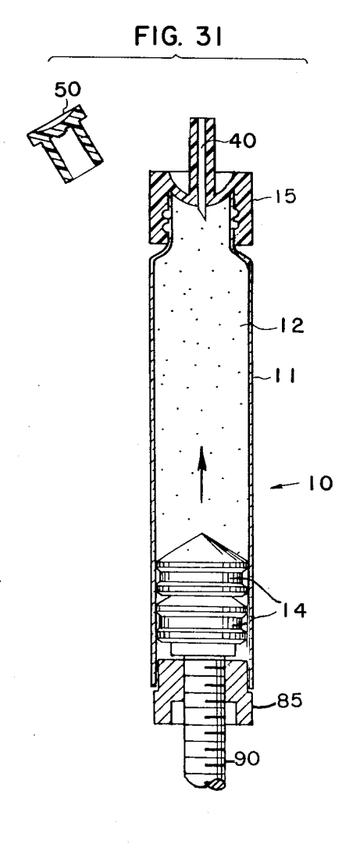
FIG. 31 is a sequential view showing the leur tip cap removed and ready for discharge.
Figure 32:
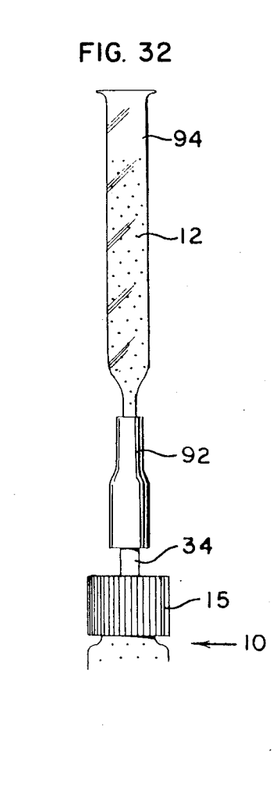
FIG. 32 is an alternative view showing the adapter for aspirating instruments secured to the leur tip cap.

The sterile needle 40 is then positioned in the syringe cartridge closure 15. This is shown in FIG. 27. Thereafter, as shown in FIG. 28, the leur tip cap 50 is positioned atop the needle 40. The plunger 90 having a thread 91 is then engaged with the thread 89 of the screw adapter 85 as shown in FIG. 29. The syringe 11 and its contents are now ready for packaging and shipment to the customer. At this point, as shown in FIG. 30 and will be described later, the lab technician mixes the contents 12 by rolling the cartridge body 11 between the palms of the hand. The metering screw plunger 90 is then turned clockwise to apply slight pressure. Thereafter, the leur tip cap 50 is depressed to insert the needle 40 through the membrane 36 of the syringe cartridge closure 15. To ready the syringe cartridge 10 for use, the leur cap 50 is removed by the lab technician as shown in FIG. 31, and the air in the needle 40 is expelled by slight rotation of the metering screw plunger 90. Where aspirating units are utilized on the instrument, as shown in FIG. 32, the aspirating adapter 92 is positioned over the top of the leur tip 34 and the contents are discharged into the aspirator 94.

Figure 33:
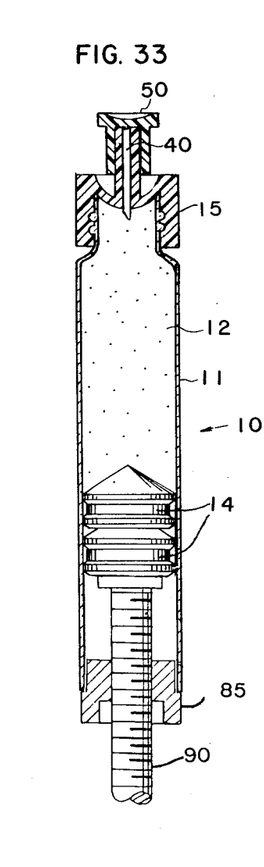
FIG. 33 is a further front elevation of the syringe cartridge with the leur tip cap replaced.
Figure 34:
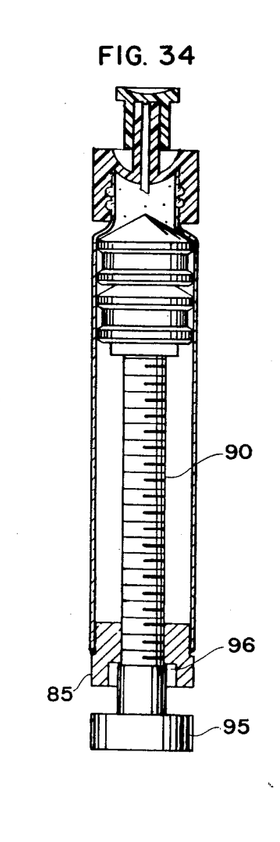
FIG. 34 is a sequential view showing a repetition of removing the contents to the point where the syringe cartridge has essentialy exhausted its contents.

Thereafter as shown in FIG. 33, the lab technician may replace the leur tip cap 50 and store the syringe cartridge 10 for further use. The previous steps are repeated, until the contents 12 are essentially all discharged from the syringe cartridge 10 as shown in FIG. 34. At this point the plunger head 95 and its associated stop 96 engage the screw plunger adapter 85, and the syringe cartridge 10 is exhausted and discarded.

Figure 35A:
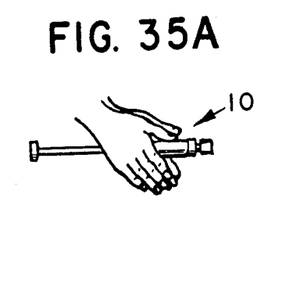
FIGS. 35A through 35F diagramatically show the hands of the lab technician manipulating the syringe cartridge.
Figure 35B:
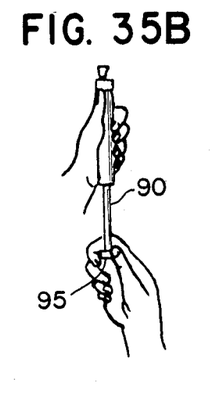
Figure 35C:
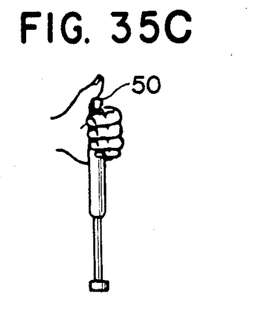
Figure 35D:
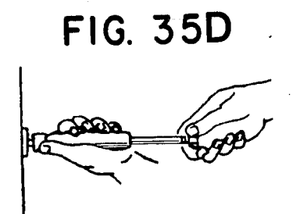
Figure 35E:
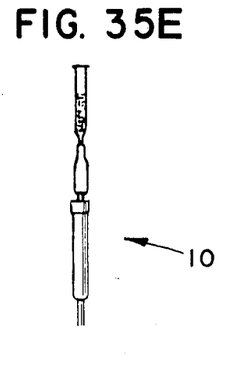
Figure 35F:
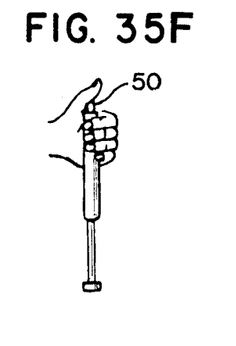

Summarizing the procedure for use, it will be seen in FIG. 35A that the syringe cartridge 10 is mixed by rolling the same between the palms of the hands of the technician. Thereafter, as shown in FIG. 35B, a slight pressure is applied to the pistons 14 by rotating the metering screw plunger 90 at its plunger head 95. As shown in FIG. 35C, the closure is then punctured by pressing down on the tip cap 50 with the thumb, the needle 40 having already been inserted. Thereafter the plunger head 95 is rotated as shown in FIG. 35D to inject the contents 12 into an instrument. Alternatively the adapter for aspirating instruments is employed as shown in FIG. 35E. Between are caps of insertion of the contents either by way of aspirating instruments or direct injection, the leur tip cap 50 is recapped as shown in FIG. 35F.

The method of filling the first embodiment is primarily illustrated in FIG. 3. This presupposes, however, that a cartridge 11 has been provided with a plunger piston 14. As noted, the contents 12 are filled until a discrete level 32 has been reached, at a predetermined volume for displacement by the closure. The closure is then applied in such fashion that a small portion of the contents will flow into a trap so that when this position of the contents dry, it will not be seen about the closure. The whole procedure is accomplished in such a fashion that zero head space remains between the contents 12 and the lower portion of the closure 15. The method for usage contemplates a leur tip cap which can be pressed downwardly and insert a dispensing needle through a diaphragm in the closure, and can be resealed by replacing the leur tip cap.

Figure 22:
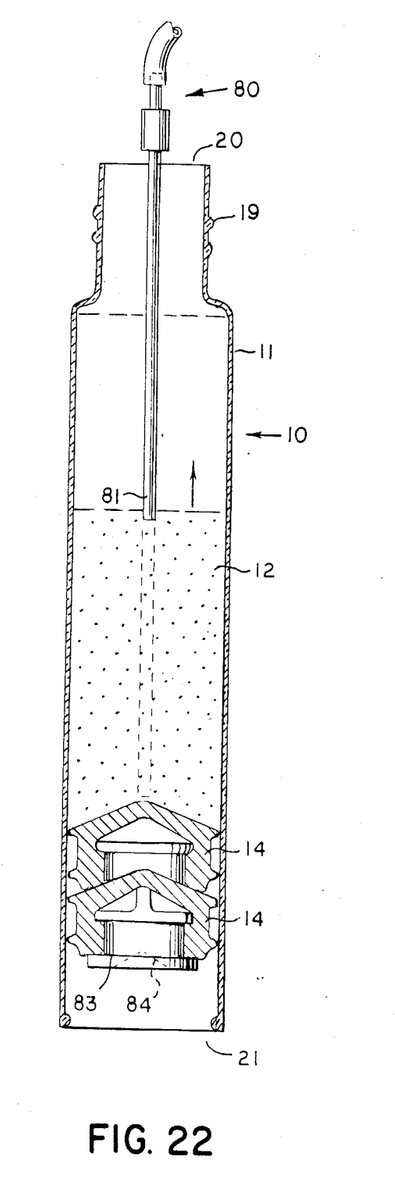
FIG. 22 is a partially diagramatic front elevation of the micrometering embodiment showing the utilization of the bottom up filler and the plungers and insert in cross-section.

In the second micrometering embodiment, as shown particularly in FIGS. 21-35, and more specifically FIGS. 22 and 23, prior to filling it is highly desirable to siliconize the interior of the cartridge body 11 before inserting the components and sterilizing. Thereafter it is flushed with a nitrogen or other inert gas prior to filling. Filling is accomplished with a bottom-up filler 80 having a discharge end 81 which fills the contents 12 into the cartridge body 11 from the bottom until it reaches a height of approximately 90%. Thereafter with a top off assembly, the balance is filled utilizing a 360° drawback system as shown in FIG. 23. Finally, the cap 15 is closed, as shown in FIG. 24, to provide for zero head space at which time the unit has the screw plunger adapter 85 positioned at the lower portion of the cartridge body 11 (FIG. 25), and a label 82 applied (FIG. 26), desirably with an underneath shrink portion which seals the screw adapter 85 in place.

While the embodiment described is directed to a blood gas control medium, where other reagents are used which are not reactive to certain inert gases, zero head space is not essential. Then a small amount of gas, such as nitrogen, can be applied after filling. Then the closed cartridge does not require zero head space. A 0%-5% head space is then filled with an inert gas.

Although particular embodiments of the invention have been shown and described in full here, there is no intention to thereby limit the invention to the details of such embodiments. On the contrary, the intention is to cover all modifications, alternatives, embodiments, usages and equivalents of the subject invention as fall within the spirit and scope of the specification and the appended claims.

I claim:

1. A syringe comprising, in combination:
   a cylindrical cartridge having two open ends,
   a movable plunger means for closing one end of the cartridge,
   a first closure means for the other end of the cartridge for displacement of product within the cartridge to achieve a predetermined head space therein,
   a second closure means removably secured to said first closure means,
   said second closure means having reseal means interacting with said first closure means to reseal with predetermined head space by displacing a portion of product in the first closure means,
   a screw plunger adapter applied at the lower portion of the cartridge, and
   a metering screw plunger adapted to engage the screw plunger adapter,
   whereby the technician may rotate the threaded metering screw plunger to advance the movable plunger means and, with precision, meter the contents for removal through the hollow bore of the needle.

2. A syringe cartridge comprising, in combination:
   a cartridge of elongate cylindrical configuration having two open ends,
   a plunger piston sealing the lower open end of said cartridge,
   a means for advancing the plunger piston,
   a syringe cartridge closure secured to the upper open end of the cartridge,
   a leur tip having a dispensing end extending from said closure,
   a leur tip cap proportioned to reclosably cover the dispensing end of the leur tip,
   a leur tip bore centrally and longitudinally of the leur tip,
   a diaphragm at the lower portion of said leur tip bore and closing the same to contents of the cartridge,
   an inverted dome at the lower portion of the closure defining a predetermined head space relationship between the closure, cartridge, and contents,
   the leur tip cap being porportioned for positioning over the leur tip,
   a plunger shaft for engaging the plunger piston and forceably ejecting the contents of the cartridge through the hollow bore in the needle,
   a second plunger adapter positoned at the lower portion of the cartridge,
   a plunger metering screw, said plunger metering screw being threadally engaged with the screw plunger adapter,
   whereby the technician may threadally rotate the metering screw plunger and, with precision, meter the contents.

* * * * *